United States Patent [19]

Fletcher et al.

[11] 4,429,373
[45] Jan. 31, 1984

[54] DATA ANALYZING SYSTEM FOR CLINICAL SPECTROPHOTOMETER

[76] Inventors: Taylor C. Fletcher, 1534 Sunny Crest Dr., Fullerton, Calif. 92635; Neal P. Flora, 10870 Holmes Ave., Mira Loma, Calif. 91752

[21] Appl. No.: 301,739

[22] Filed: Sep. 14, 1981

[51] Int. Cl.³ .......................................... G01N 33/16
[52] U.S. Cl. ........................................ 364/900; 422/55
[58] Field of Search .................. 364/200, 900, 701; 422/55, 65; 73/23.1

[56] References Cited

U.S. PATENT DOCUMENTS

| | | | |
|---|---|---|---|
| 3,662,163 | 5/1972 | Miller et al. | 364/701 |
| 3,748,044 | 7/1973 | Liston | 356/409 |
| 3,757,306 | 9/1973 | Boone | 364/200 |
| 3,860,393 | 1/1975 | Campen | 73/23.1 |
| 4,049,953 | 9/1977 | Evans | 364/701 |
| 4,064,395 | 12/1977 | Schubeler et al. | 364/900 |
| 4,122,518 | 10/1978 | Castleman et al. | 364/900 |
| 4,135,883 | 1/1979 | McNeil et al. | 422/55 |
| 4,138,718 | 2/1979 | Toke et al. | 364/900 |
| 4,138,735 | 2/1979 | Allocca et al. | 364/900 |
| 4,141,078 | 2/1979 | Bridges et al. | 364/900 |
| 4,149,235 | 4/1979 | Froyd et al. | 364/900 |
| 4,153,945 | 5/1979 | Actor et al. | 364/900 |
| 4,158,227 | 6/1979 | Baxter et al. | 364/200 |
| 4,168,955 | 9/1979 | Allington | 422/65 |
| 4,188,664 | 2/1980 | DeShon | 364/200 |
| 4,224,032 | 9/1980 | Glover et al. | 422/65 |
| 4,229,804 | 10/1980 | Kobayashi et al. | 364/900 |
| 4,234,926 | 11/1980 | Wallace et al. | 364/900 |
| 4,293,917 | 10/1981 | Wasserman | 364/701 |

Primary Examiner—Jerry Smith
Assistant Examiner—Jameson Lee
Attorney, Agent, or Firm—Keith D. Beecher

[57] ABSTRACT

A microprocessor controlled data analyzing system is provided for use with a clinical spectrophotometer, such as the Abbott Bichromatic Analyzer (ABA-100), which is used for testing samples of serum derived from patients' blood. The data analyzing system of the invention serves to analyze the outputs from the spectrophotometer, and to transform the outputs into reportable units. The data analyzing system is capable of providing the operator with full instructions as to any particular test and to control the spectrophotometer to perform such a test.

4 Claims, 13 Drawing Figures

FIG. 3

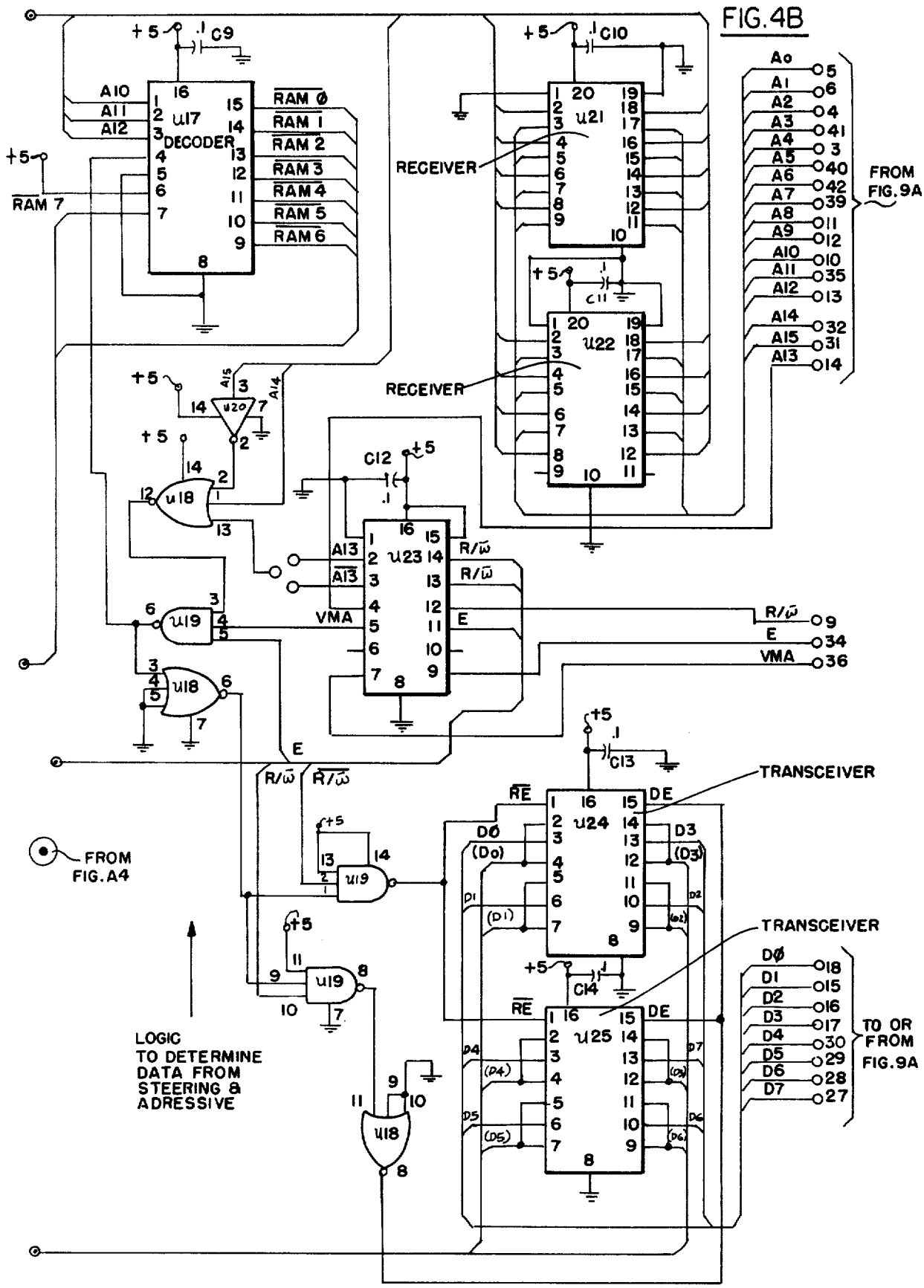

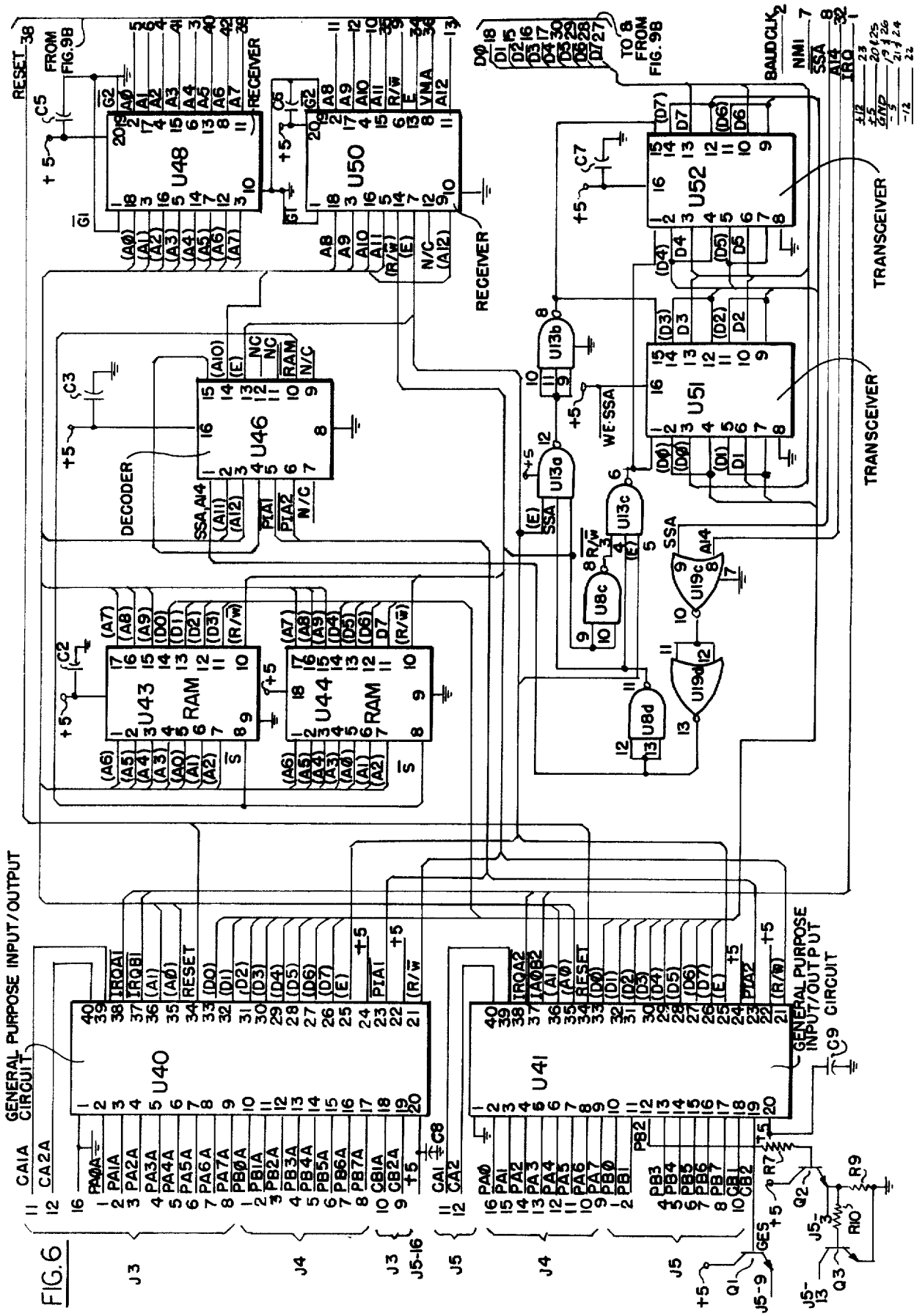

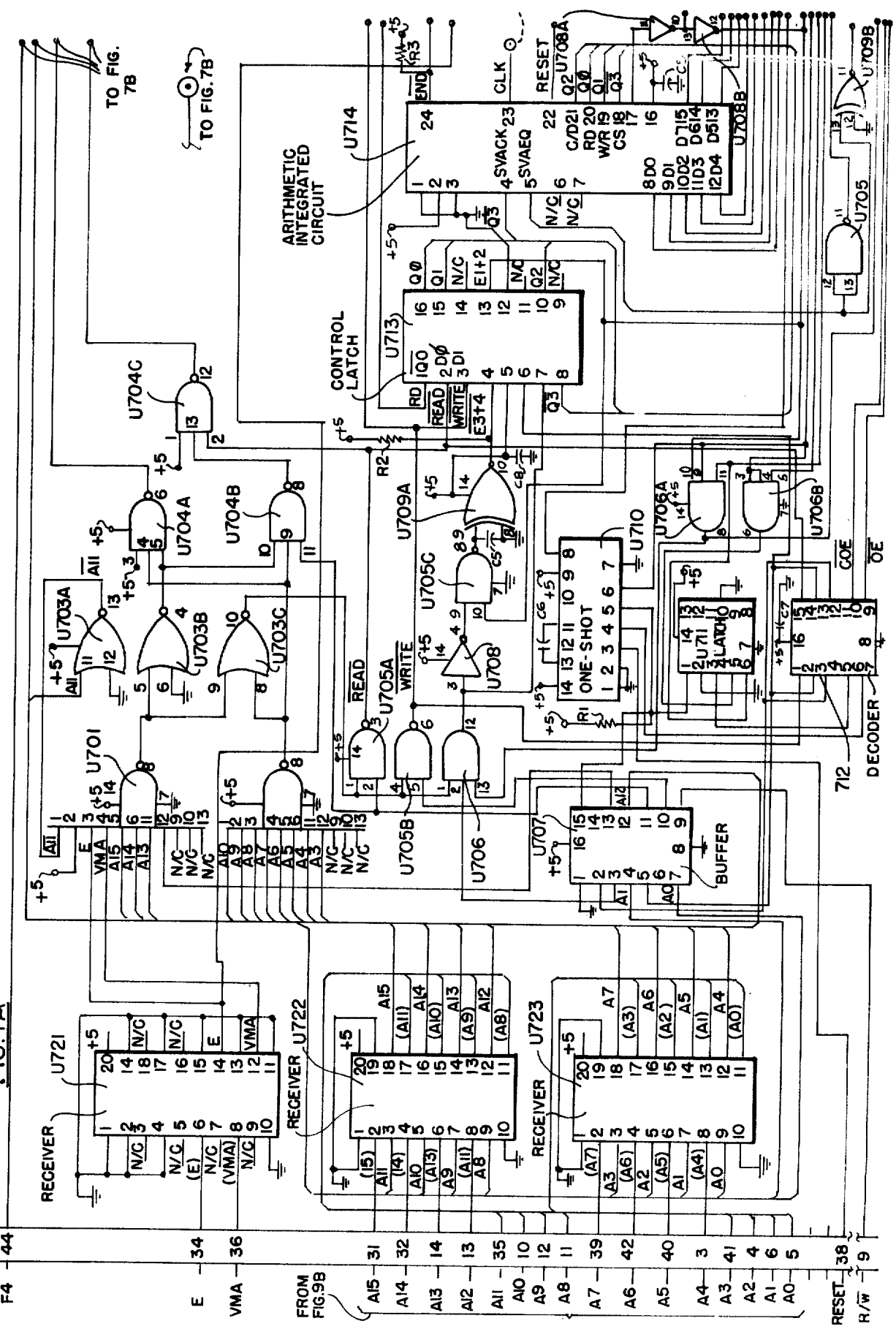

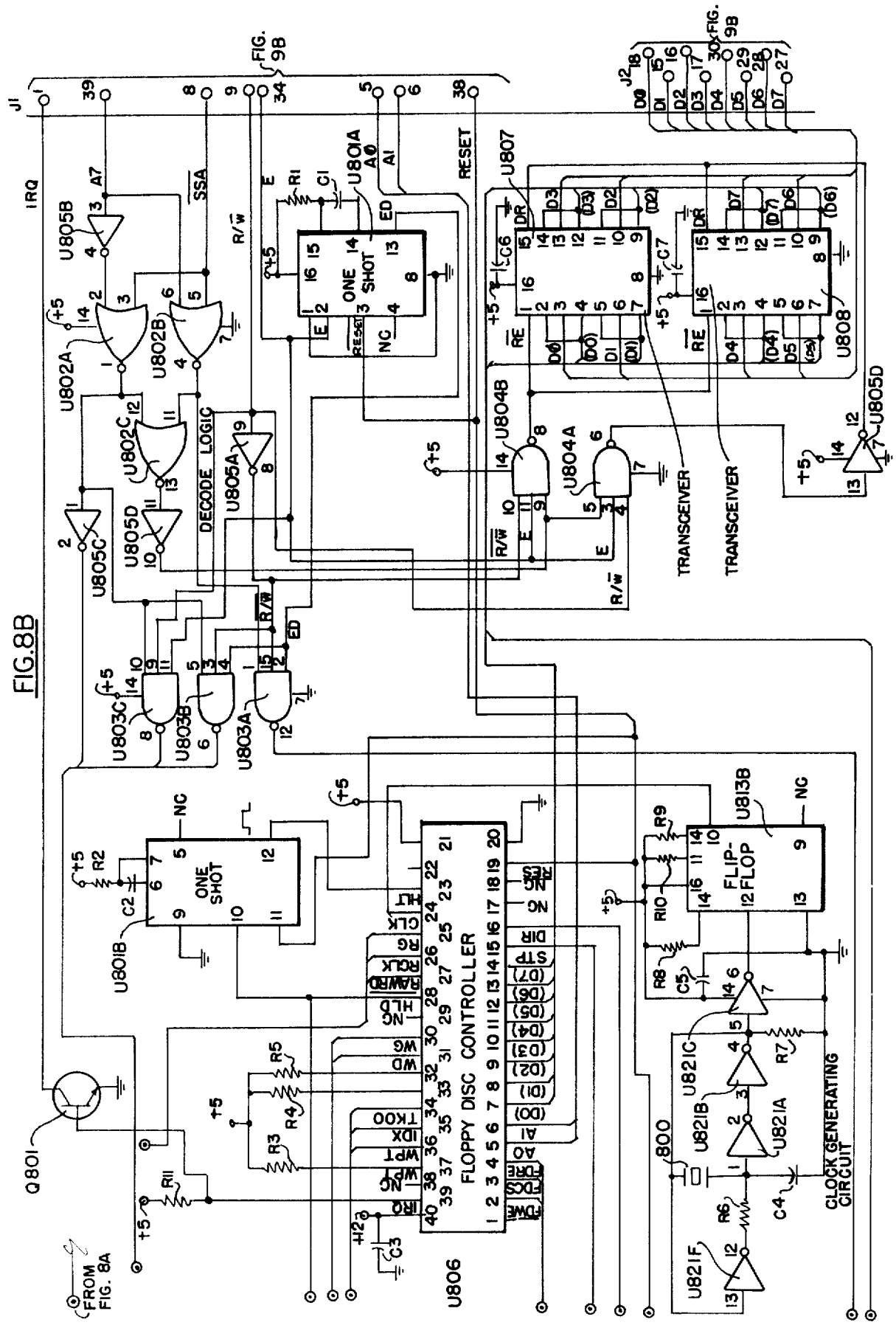

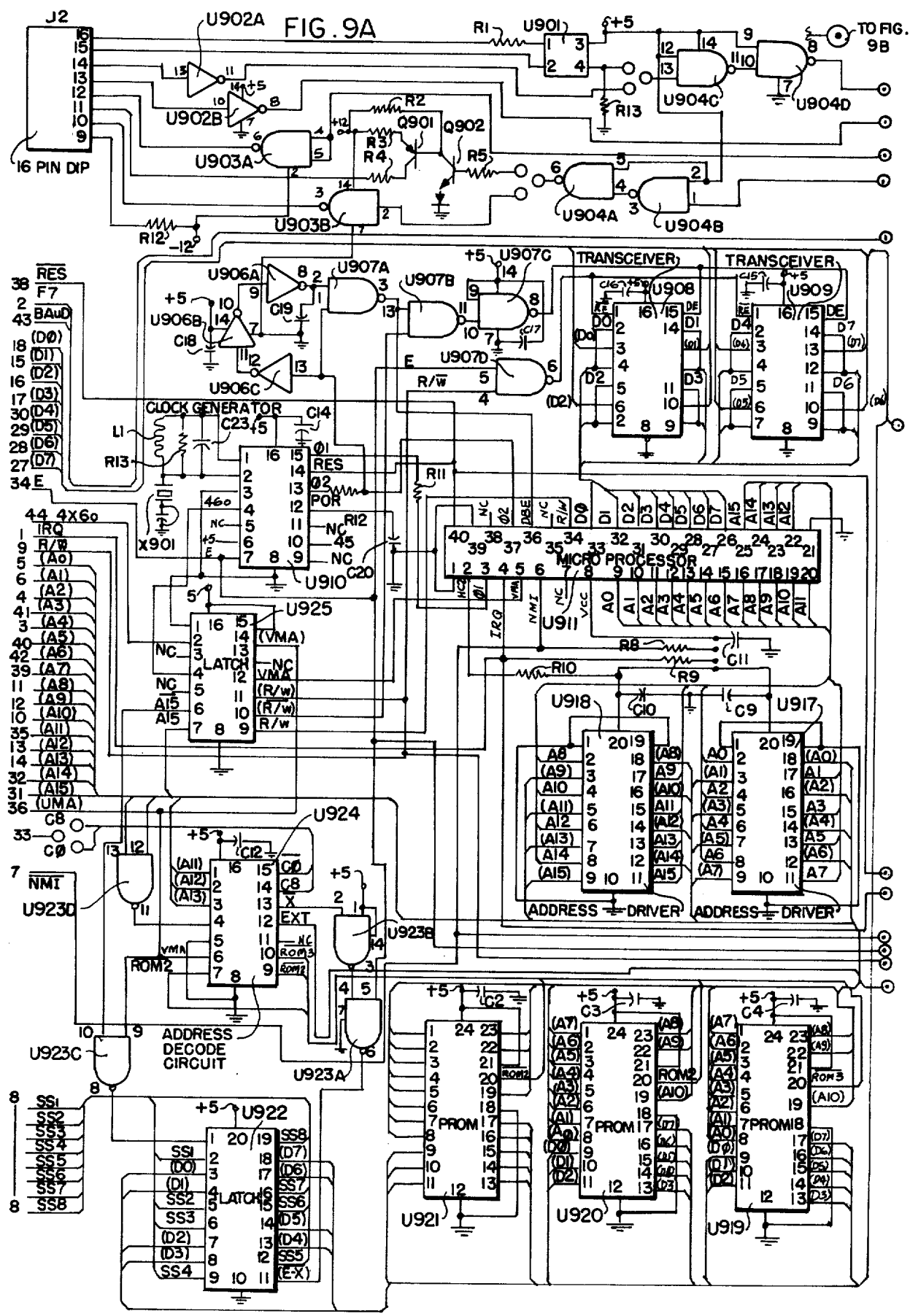

DATA ANALYZING SYSTEM FOR CLINICAL SPECTROPHOTOMETER

BACKGROUND

Spectrophotometric analysis is a method of chemical analysis based on the absorption by a particular impurity in a sample under test of light of a specific wavelength. The instruments used for spectrophotometric analysis are known as spectrophotometers, and these instruments are capable, by selecting different wavelengths of light of measuring the percent concentration of various known impurities in the sample. Spectrophotometers are in present-day widespread use for clinical purposes, for testing serum derived from the blood of patients. The Abbott Bichromatic Analyzer (ABA-100) referred to above represents such a clinical spectrophotometer.

A simple spectrophotometer consists of a source of light, a monochromator containing a prism or grating which disperses the light so that only a limited wavelength, or frequency range, is allowed to irradiate the sample or specimen, the sample itself, and a detector, such as a photocell which measures the amount of light transmitted by the sample to provide a reading of the "absorbance" of the sample. The sample is placed in a small cell or "cuvette" as the cell is called, the walls of which are transparent at the wavelength of light being used, and the cuvette is interposed between the surface of light and the photocell.

The ABA-100 is described in U.S. Pat. No. 3,748,044. It is a system for analyzing reactions that take place within a plurality of individual specimens. According to a principal feature of the ABA-100 system, a dispenser is provided that transfers specimens to a disposable cuvette for holding each of the specimens in an individual compartment. Analyzing means are also used to generate and transmit a beam of radiant energy through the specimens. This mode of operation produces an analysis signal having a value proportional to a property of a predetermined specimen each time the beam passes through that specimen.

Each time the beam passes through a specimen, address means generate an identity code that uniquely identifies that specimen. Cycling means are employed for causing the beam to separately pass through each of the specimens during multiple cycles of operation. For example, during a first cycle of operation, a first set of analysis signals having a first set of values corresponding to the specimens may be created. Likewise, during a second cycle of operation, a second set of analysis signals having a second set of values may be created. Memory means for instantaneously storing the values of the analysis signals at addresses corresponding to the predetermined specimens are also utilized. Electronic processing means are used in the ABA-100 system to enable the cycling means and memory means, as well as to compare the values stored in the memory means with additional values created by the analyzing means in order to evaluate the reactions taking place in the specimens.

For example, in order to determine the rate at which relatively slow reactions take place within each of the specimens, the memory means in the ABA-100 system are used to store the first set of values created during a first cycle of operation. Then, while the second cycle of operation is creating the second set of values, processing means compares the values of the first and second sets of values which correspond to the same specimen. In this way, the rates of reaction of all the specimens are determined during the same period of time.

In order to determine the rate at which a rapid reaction takes place within a predetermined specimen in the ABA-100 system, beams of radiant energy are passed through the predetermined specimen at specified short intervals, such as every 15 seconds. This mode of operation results in a set of time-spaced analysis signals that are sequentially stored in the memory means of the ABA-100. The processing means in the ABA-100 then compares the value of each succeeding analysis signal with the value of a previous analysis signal stored in the memory means. In this manner, the rate of the reaction may be accurately determined over short time intervals.

In order to analyze an end point determination by the ABA-100 system, one of the specimens comprises a known concentration of the substance, and other specimens contain unknown concentrations of the substance. The value corresponding to the known concentration is stored in the memory means of the ABA-100 and other values corresponding to the unknown concentrations are compared with the value stored in the memory means by the ABA-100 processing means.

According to another feature of the ABA-100 system, two wavelengths of radiant energy are generated. The first wave length lies substantially in the center of a predetermined band; and the second wavelength is greater than the first wavelength and lies substantially outside the predetermined band. The radiant energy at the two wavelengths is then sequentially transmitted through the specimens along a single path and is compared in the manner described. According to this feature, the transmission of radiant energy is also interrupted periodically in order to establish a reference level. By using the ABA-100 system, the concentration of a predetermined substance is determined instantaneously with a degree of accuracy heretofore unattainable.

The ABA-100 is capable, for example, of providing an analog output representing the optical transmission of each of a plurality of serum specimens at the selected wavelength, depending upon which test is being conducted. The data analyzing system of the invention may provide outputs representative of percent concentration which has a linear relationship with optical density, so that the percent concentration of the particular impurity may be indicated directly by the system.

As mentioned above, the data analyzing system of the invention is intended to operate in conjunction with a clinical chemistry analyzer spectrophotometer such as the ABA-100 system. The data analyzing system of the invention is capable, inter alia, of directing the sequence of operations of the ABA-100 for any particular test, to perform control statistics, of calibrating results of all types of assays made by the ABA-100, and of printing these results directly into reportable units. The system of the invention is capable of making defined calculations for end point assays, rate reactions, EMIT assays, and specific reactions such as T4.

The data analyzing system of the invention automatically flags out-of-limit data. For each test, the operator can set the standard tolerance and normal range, and the system prints error flags if, for example, the result exceeds the entered normal high range value (NRHI); or if the result is lower than the entered normal low range value (NR LOW), or if any of the standards exceed the entered standard tolerance (TOL).

The data analyzing system of the invention is capable of automatically controlling the ABA-100, and it can, for example, trigger the auxiliary dispenser of the ABA-100 automatically at any carousel station. Moreover, the data analyzing system of the invention can direct the sequence of operations, and it can list all test variables for any test as well as carousel load lists. The system can also perform quality control statistics, specifically, for each test run, the control mean, standard deviation, and coefficient of variation can be printed.

BRIEF DESCRIPTION OF THE DRAWINGS

FIG. 3 is a block diagram of the data analyzing system of the present invention in one of its embodiments;

FIGS. 4A and 4B are schematic diagrams of a random access memory circuit contained within the data analyzing system of the invention;

FIG. 6 is a circuit diagram of a circuit for interfacing the data analyzing system of the invention with the ABA-100 bichromatic analyzer;

FIGS. 7A and 7B are schematic circuit diagrams of an arithmetic processor which is included in the data analyzing system;

FIGS. 8A and 8B are schematic representations of a controller circuit for a floppy disc memory included in the system of the invention; and FIGS. 9A and 9B are schematic diagrams of a microprocessor master circuit which is included in the data analyzing system of the invention.

DETAILED DESCRIPTION OF THE ILLUSTRATED EMBODIMENT

Figure 1:
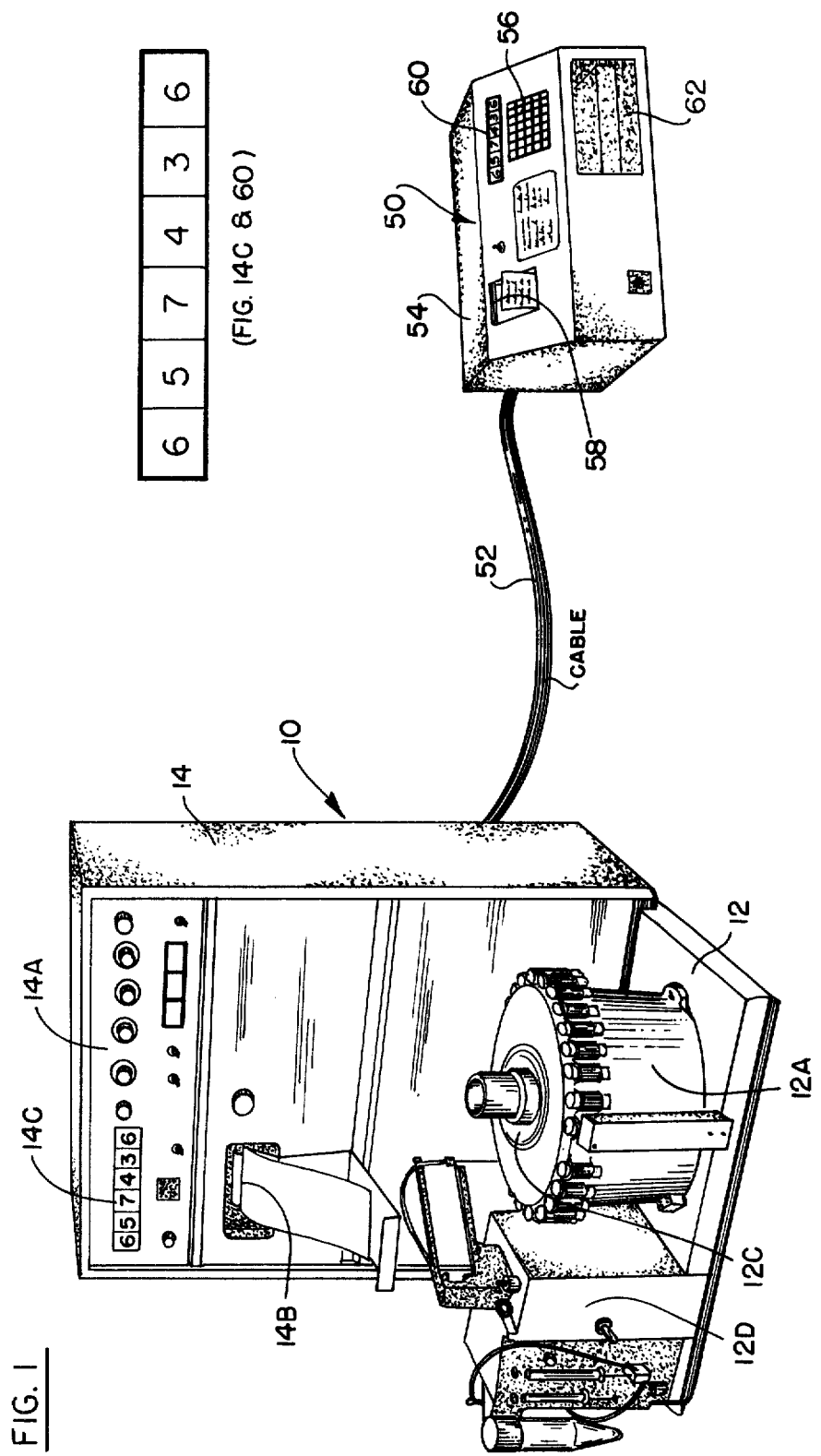
FIG. 1 is a perspective representation of the Abbott Bichromatic Analyzer System, designated (ABA-100), which is described in U.S. Pat. No. 3,748,044, and which is presently on the market; and a data analyzing system incorporating the concepts of the present invention, which is connected to the ABA-100.

The ABA-100 bichromatic analyzer 10 shown in FIG. 1 consists of two basic modules, a processing module 12 which performs the manipulative procedures associated with an actual analysis, and a control module 14 which processes the electrical data generated during the analysis. The control module 14 includes a control panel 14A, computer and electronic circuitry, a printer 14B, and a data display panel 14C.

The main components of the processing module 12 include a cylindrical housing 12A in which the photometric process is carried out, a rotatable cylindrical carousel 12B which is mounted coaxially with the housing 12A, and a disposable multi-cell cuvette 12C which is mounted in the center of the carousel. The carousel carries a plurality of serum specimens in individual containers about its periphery, and the cuvette provides a corresponding number of transparent cells. The transparent cuvette cells are successively placed in the light path of the photometer contained within housing 12A as the carousel rotates. The processing module also includes a dispenser 12D which serves to transfer the serum sample from one of the containers on the carousel and a selected reagent to a corresponding cell of the multi-cell cuvette, and to repeat this operation for each of the serum containers as the carousel rotates.

The ABA-100, as explained briefly above, may be operated in an end-print assay mode, a normal kinetic rate assay mode, or a fast kinetic rate assay mode. For end-point determination, the absorbance ($A_d$) of cuvette cell #1 (Reagent Blank) is subtracted from the absorbance of subsequent cuvette cells, and for normal operation of the ABA-100, without the data analyzing system of the present invention, the net result is printed out by printer 14B, either in absorbance units or, if an appropriate calibration factor has been entered into the internal computer of the ABA-100, in concentration units, or other reportable units.

As described in detail in U.S. Pat. No. 3,748,044, during the normal kinetic rate reaction mode, the absorbance readings made during the second revolution of the carousel for the reaction mixture in each cell of the multi-cell cuvette 12C are placed in the memory of the ABA-100 computer, and these readings are subtracted from the readings for the third revolution of the carousel. The results represent the reaction rate for a programmed time period, and these rate measurements may be continued from revolution-to-revolution of the carousel. In each instance, when the ABA-100 is used alone, and not in conjunction with the data analyzing system of the present invention, the results are displayed by display 14C, and printed out by printer 14B.

For the fast kinetic rate reaction mode, each cell of the multi-cell cuvette remains in the light path of the photometer in the cylindrical housing 12A for one or two minutes, depending upon whether a 15 second measurement or a 30 second measurement is being made. In either case, three rate measurements are made for each reaction mixture in the respective chambers of the cuvette. With this capability, enzyme assays can be performed in highly active samples under zero order conditions.

Figure 2:
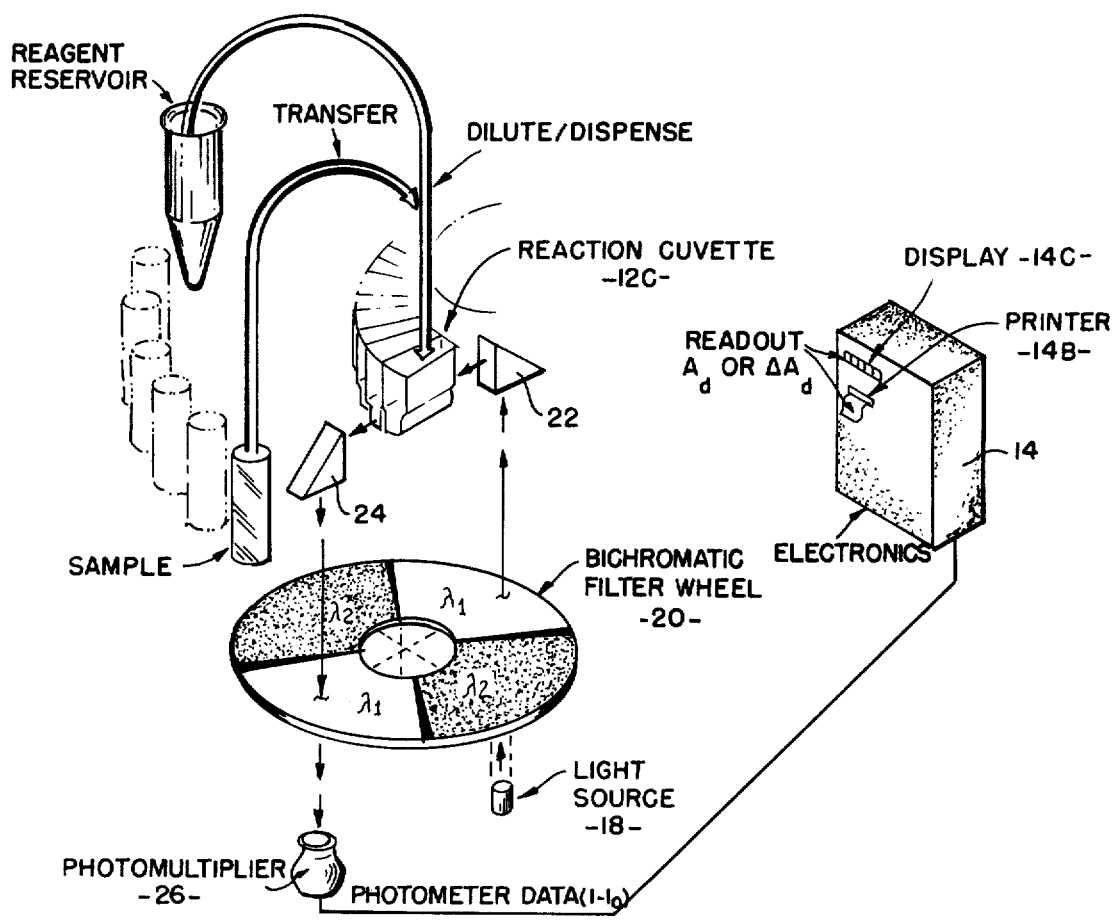
FIG. 2 is a functional diagram of the Abbott Bichromatic Analyzer System (ABA-100)

The functional design for the ABA-100 is shown in FIG. 2, which shows how each specimen is sampled from a disposable container on the carousel and dispensed with a predetermined volume of reagent, and mixed in a corresponding cell of the multi-cell cuvette 12C. After a selected incubation interval, the mixture in the particular cuvette chamber is examined in the cylindrical housing 12A (FIG. 1) in a bichromatic light sequence from light source 18 and filter wheel 20, as the light is passed through prisms 22 and 24, and the output from photomultiplier 26 is processed in control unit 14.

As stated above, three distinct modes of operation are available in the ABA-100. The end-point mode identifies an assay of a reaction which reaches equilibrium; the normal kinetic mode defines an assay in which the reaction rate is to be determined; and the fast kinetic mode defines an assay run in speeded-up sequence to provide resolution of rapid reaction rates. These modes are set forth in the following table:

| OPERATION MODE | CAROUSEL REV. NO. | DISPENSE* | READING DISPLAY* | PRINT* | RED PRINT** | REMARKS |
|---|---|---|---|---|---|---|
| End-point | 00+ | No | No | No | — | |
| | 1 | Yes | No | No | — | |

-continued

| OPERATION MODE | CAROUSEL REV. NO. | DISPENSE* | READING DISPLAY* | PRINT* | RED PRINT** | REMARKS |
|---|---|---|---|---|---|---|
| | 2,3,4, and > 4 | No | Yes | Yes | No | See (a) below |
| Normal | 00+ | No | No | No | — | |
| Kinetic | 1 | Yes | No | No | — | |
| | 2 | No | Yes | No | — | See (b) below |
| | 3 | No | Yes | No. Yes | See (c) | below |
| | 4 and > 4 | No | Yes | Yes | Yes | See (c) below |
| Fast Kinetic | 00+ | Yes | No | No | — | See (d) below |
| | 1 | Yes | Yes | Yes | No | See (e) below |

*Suppressed when sample container space is empty.
**Applicable to kinetic reactions in the down direction in the normal kinetic mode.
+Refers to starting position before revolution No. 1 is displayed on Nixie panel.
(a) Absorbance, with or without calibration factor, for reaction cell No. 1 (reagent blank) entered into memory for each revolution and subtracted from subsequent values.
(b) All absorbance readings entered into memory.
(c) Absorbance reading from previous revolution is subtracted and resulting $\Delta A_d$ is printed. The $\Delta A_d$ for the substrate control in cuvette No. 1, which may be due to substrate degradation, evaporation, and instrument drift, is automatically subtracted from all other $\Delta A_d$ measurements in each revolution.
(d) Dispensing will occur before revolution Mo. 1 is displayed. Revolution No. 1 will be displayed at the end of the pre-incubation period for the first sample. Dispensing will continue with no change in timing.
(e) Four readings at 15 or 30 second intervals, as selected, result in three $\Delta A_d$ printouts by subtraction of previous readings.

For kinetic studies, absorbance ($A_d$) in each active cell of the multi-cell cuvette is computed from photomultiplier data and stored in the memory of the ABA-100 computer during the first reading cycle. The second reading cycle consists of the computation of $A_d$ and in obtaining the difference between that value and the reading from the previous cycle resulting in the desired $\Delta A_d$. In the third and fourth readings, the $\Delta A_d$ is obtained from the difference between the prior $A_d$ and the current $A_d$. Any rate change in the substrate control cuvette over a time interval is automatically determined and subtracted from all subsequent rate measurements for each revolution of the carousel.

The ABA-100 is capable of performing the following standard methodologies.

| | Filter | Operating Mode | Reaction Direction | Analysis Time | Carousel Revolutions | Temp | Dilution Ratio | Sample Size | Calibration Factor | Page Reference |
|---|---|---|---|---|---|---|---|---|---|---|
| SGOT (Serum glutamic oxaloacetic transaminase) | 340/380 nm | Rate | DOWN | 5 min | 4 | 37° C. | 1:51 | 5 µl | (a) | 3-19 |
| SGPT (Serum glutamic pyruvic transaminase) | 340/380 nm | Rate | DOWN | 5 min | 4 | 37° C. | 1:51 | 5 µl | (a) | 3-23 |
| CPT (Creatin phosphokinase) | 340/380 nm | Rate | UP | 5 min | 4 | 37° C. | 1:51 | 5 µl | (a) | 3-27 |
| LDH—L (Latic dehydrogenase)* | 340/380 nm | Rate | UP | 5 min | 4 | 37° C. | 1:51 | 5 µl | (a) | 3-31 |
| α-HBD (α-hydroxybutyric dehydrogenase) | 340/380 nm | Rate | DOWN | 5 min | 4 | 37° C. | 1:101 | 5 µl | (a) | 3-35 |
| Alk. Phos. (Alkaline Phosphatase) | 415/450 nm | Rate | UP | 5 min | 4 | 37° C. | 1:51 | 5 µl | (b) | 3-39 |
| Glucose | 340/380 nm | End-point | UP | 5 min | 2 | 37° C. | 1:101 | 5 µl | (c) | 3-43 |
| BUN (Blood urea nitrogen) | 340/380 nm | End-point | DOWN | 5 min | Infinity (∞) (e) | 37° C. | 1:101 | 5 µl (d) | (c) | 3-47 |

*Lactate substrate
(a) Obtained from 51,000/filter factor. Filter factor will be approximately 5.0 and setting will be approximately 1020. for International Units per liter at 37° C. For spectrophotometric units this must be multiplied by 2.07 to yield a calibration factor of approximately 2111.
(b) To be defined.

(c) Derived from $\left( \frac{\text{Conc. (std)}}{A_d \text{(std)}} \right) \times 0.5$. Approximately 192.5 for glucose, and 156.0 for BUN.

(d) The sample is a 1:10 dilution of serum. Diluent may be distilled water or normal saline. Diluent must be ammonia-free, and environmental air should not be contaminated with ammonia.
(e) Results may be read after 20 minutes of incubation (five carousel revolutions). Color is stable up to 12 carousel revolutions.

During normal operation of the ABA-100, and as described in detail in U.S. Pat. No. 3,748,044, the display panel 14C displays, and the printer 14B prints the absorbance $A_d$ for end-point assays, and the absorbance differential $\Delta A_d$ for kinetic studies. For the end-point assays, absorbance $A_d$ is computed from the photometer data $(1-I_0)$ from photomultiplier 26, first in the reagent blank cell and subsequently in each active cell in succession. The absorbance $A_d$ from the reagent blank cell is stored in the computer memory of the ABA-100, and is subtracted from each active reading to give a reagent blank correction. The corrected $A_d$ is displayed by display 14C, and is printed out by printer 14B, as it is computed.

The data analyzing system of the present invention is designated 50 in FIG. 1, and the system is shown as connected to the ABA-100 Bichromatic Analyzer by an electric cable 52. As explained above, the purpose of the system of the present invention is to control the operation of the ABA-100, and other similar instruments, for selected serum tests.

The data analyzing system 50 of the invention is mounted in a housing 54, and it includes a key pad 56, a printer 58, and a display panel 60, and a floppy disc drive 62. Display panel 60 may include a 16-character alphanumeric display; printer 58 may be a 20-column alphanumeric printer; and the floppy discs received in drive 62 may be non-volatile 80 kilobyte, 5¼ inch, single side, single density recording discs.

The data analyzing system of the invention can be used to control the ABA-100, and other similar instruments, to enable such instruments to perform all the tests set forth in the above table; as well as to run EMIT assays and T4's, as mentioned above. As also previously noted, the data analyzing system is capable, inter alia, of directing the sequence of operations of the bichromatic analyzer instruments for any particular test, of performing control statistics, of converting absorbance units directly into EMIT units, and of flagging out-of-limit date.

Figure 3:
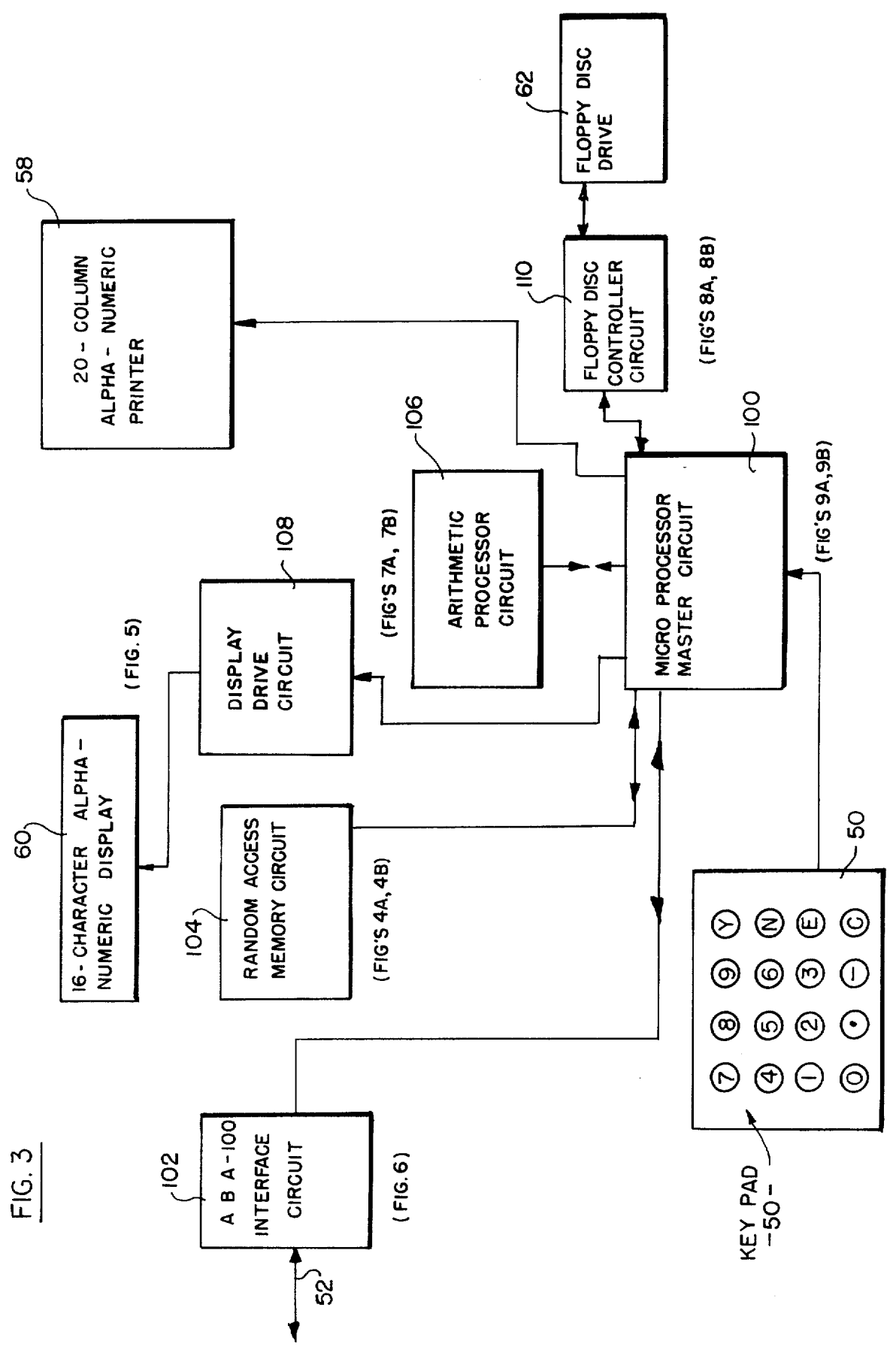

A block diagram of the data analyzing system 50 of FIG. 1 is set forth in FIG. 3. As shown in FIG. 3, the data analyzing system 50 of FIG. 1 includes a central processing unit in the form of a microprocessor master circuit represented by block 100, and which is shown in circuit detail in FIGS. 9A and 9B. The block 100 is connected to an interface circuit 102, which is shown in circuit detail in FIG. 6, and the interface circuit serves to connect the data analyzing system to the ABA-100 of FIG. 1 by way of the cable 52.

Figure 4A:
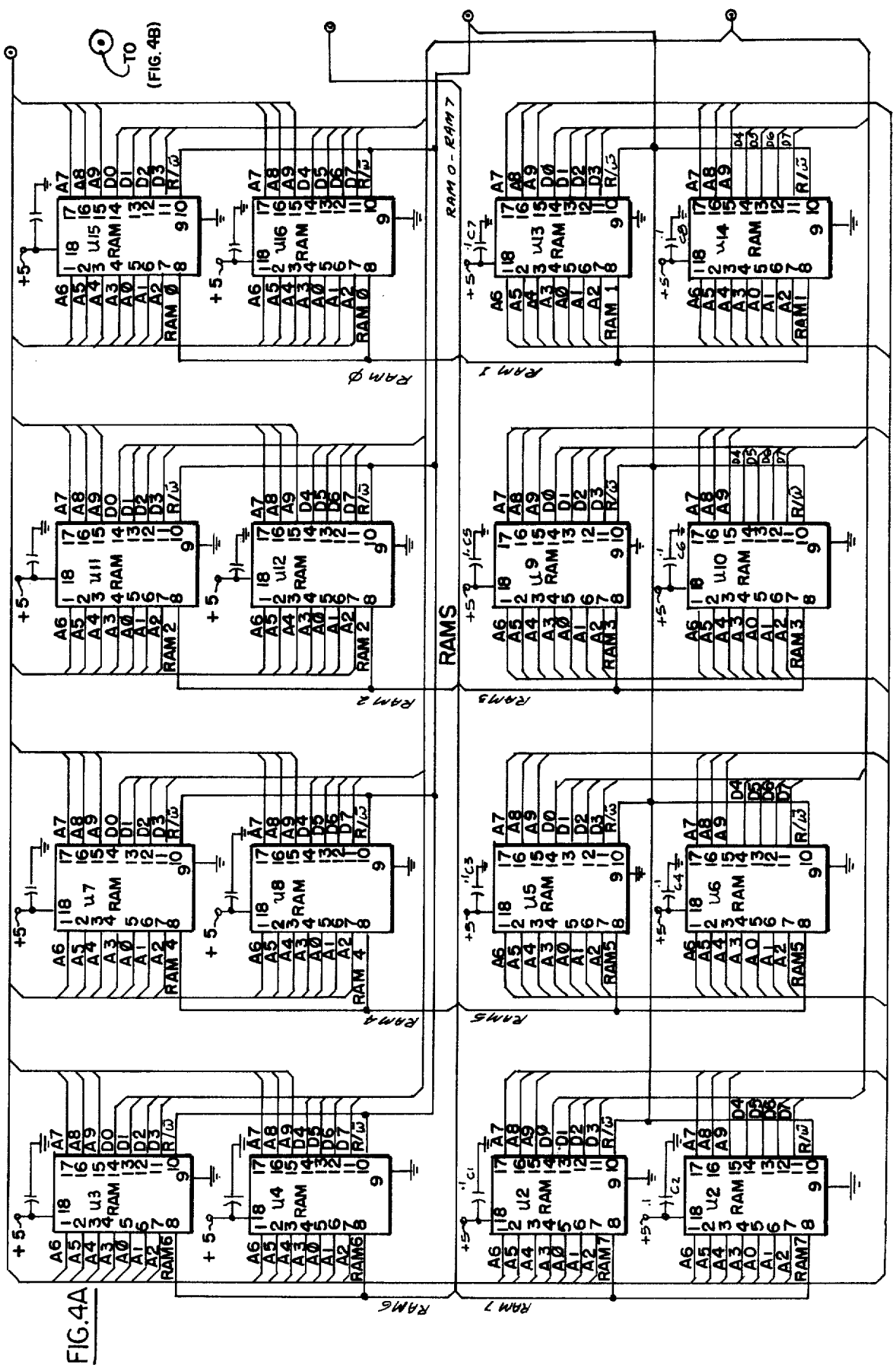

The data analyzing system 50 also includes an 8K random access memory circuit represented by block 104, and which is shown in circuit detail in FIGS. 4A and 4B. The microprocessor circuit 100 is connected to an arithmetic processor circuit 106, which is shown in circuit detail in FIGS. 7A and 7B, and it is also connected through a display drive circuit 108 to the alphanumeric display panel 60, the circuit being shown in more detail in FIG. 5.

Figure 8A:
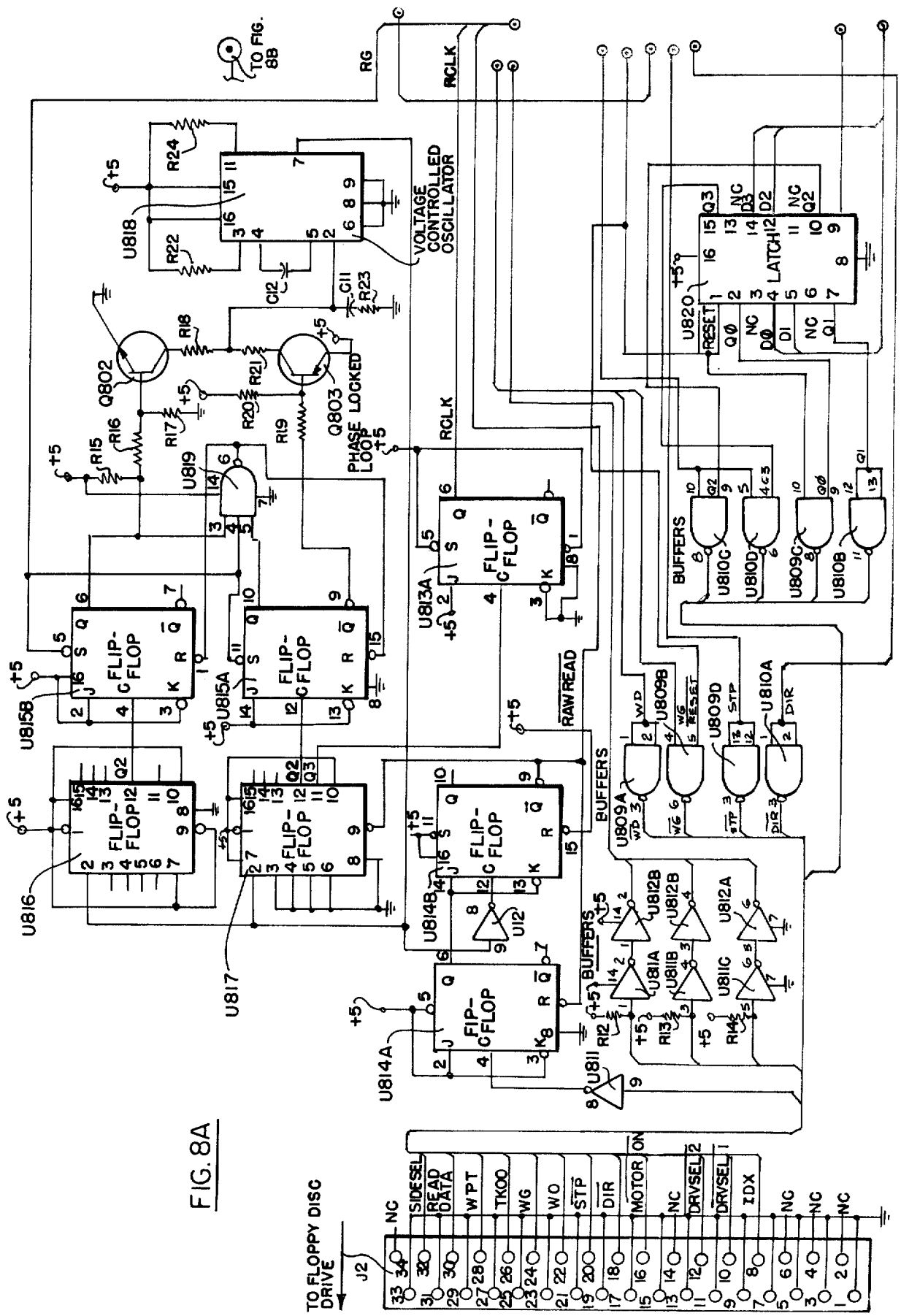

Floppy disc drive 62 is controlled by a floppy disc controller circuit 110, the details of which are shown in FIGS. 8A and 8B. The microprocessor circuit is connected to the floppy disc controller circuit. The microprocessor circuit is also connected to the printer 58, which may be a thermal printer, or any other appropriate unit. Finally, the key pad 50 is connected to the microprocessor master circuit 100, and it serves to control the master circuit in accordance with instructions entered into the key pad.

In the operation of the data analyzing system shown in block form in FIG. 3, the operator enters the particular test to be run from the standard methodologies set forth in the above table, and enters the code number corresponding to that test on the key pad. The name of the particular test then appears on the display 60, so that the operator can be sure that he has selected the proper test.

The data analyzing system then looks to the floppy disc in disc drive 62 and selects the various parameters of the particular test from the data stored on the disc, and prints out the various settings of the ABA-100 which are to be established for that test, these including the filter set, the ratio of serum to reagent, the temperature, the general category of reagent to be used, and so on. The data analyzing system also prints out information to the operator as to what cells of the multi-cell cuvette are to contain standards and/or controls, and what standards are to be used. After all of the foregoing have been established, the data analyzing system displays "start ABA", and the operator pushes a start button to commence the operation. The data analyzing system then takes over the control of the ABA-100, and receives absorbance unit readings from the ABA-100. These readings are converted, by linear or non-linear calculations into laboratory reportable units, and that data is printed out by the printer 58.

The circuitry of FIG. 4A includes 16 random access memories, each of the type designated 2114, the memories being designated U1–U16 respectively. Information is written into the random access memories, and read out of the random access memories, by the logic circuitry of FIG. 4B. The circuitry of FIG. 4B includes a pair of receivers designated U21 and U22, each of which may be of the type designated 74LS244. The receivers U21 and U22 receive the address signals $A_0$–$A_{15}$ from the master board circuit of FIG. 9A.

The receivers U21 and U22 supply the address signals $A_{10}$, $A_{11}$ and $A_{12}$ to a decoder U17 which may be of the type designated 74LS138. Decoder U17 responds to the address signals $A_{10}$, $A_{11}$ and $A_{12}$ to produce random access memory selection signals $\overline{RAM0}$–$\overline{RAM7}$, which signals select pairs of the random access memories U1–U16. The selected pairs of random access memories are then addressed by the address signals $A_0$–$A_6$ from the receivers U21, U22, and the selected pairs either generate data signals D0–D7 from the selected address, or store the data signals at the selected address, depending on the state of the read-write signal $R/\overline{W}$.

Data signals D0–D7 to be stored in the random access memories are received from the circuit of FIG. 9A by transceivers U24, U25, each of which may be of the type designated 8T26A; and data signals from the addressed random access memories are transmitted to the circuit of FIG. 9A by the transceivers U24, U25. The read-write signal $R/\overline{W}$, and signals E and VMA are received from the circuit of FIG. 9A by an inverter U23 which also may be of the type designated 8T26A.

An inverter U20 which may be of the type designated LS04; a "nor" gate U18 which may be of the type designated LS27; a "nand" gate U19 which may be of the type designated LS10; and a further "nand" gate U19 which also may be of the type designated LS10, are associated with the transceivers to form logic circuitry which determines the data flow, and which also performs steering and addressing functions.

The E signal is a master clock that tells the rest of the system when data is going to exchanged if in fact it is going to be changed. For example, if a byte of data is to be read from memory the address information is first placed on the address bus. At that time the E signal is low. Some period of time typically 270 nanoseconds later the read/write line (R/W̄) goes high. The VMA line which stands for Valid Memory Address also goes high. Now, when the E signal goes high it is considered that data is now valid for use by the central processing unit (CPU). The CPU then latches the data into its internal register. The E signal then returns to its low state, the read/write signal (R/W̄) goes to its low state, and the VMA line goes low. The complete cycle of operation is essentially clocked by the E pulse.

In general, in the operation of the circuit of FIGS. 4A and 4B, the address signals ($A_0$–$A_{13}$) are received from the receivers U21 and U22, and they are introduced to a block decoder U17 which responds to the address signals to generate selection signals which select the particular RAM's. It should be noted that only the address signals A10, A11 and A12 go to decoder U17, and the decoder in turn generates select signals which select pairs of the RAM's. The other addresses then are used to address the individual cells in the pair of RAM's selected by the block decoder U17.

The inverter U23 inverts the R/W̄ signal so that it is fed with proper polarities to the "nand" gates which operate the transceivers U24 and U25 for the read or write mode. The inverter U25 also, for example, supplies A13 and Ā13 to enable logic circuitry, so that the particular memory bank of FIGS. 4A and 4B is enabled only when the inverter causes it to be enabled. This means that the circuitry of FIGS. 4A and 4B can be used for one state of inverter A13, and an entirely different memory bank circuit can be activated for a second state of inverter A13, so that the same address signals can be used for both memory banks.

Figure 5:
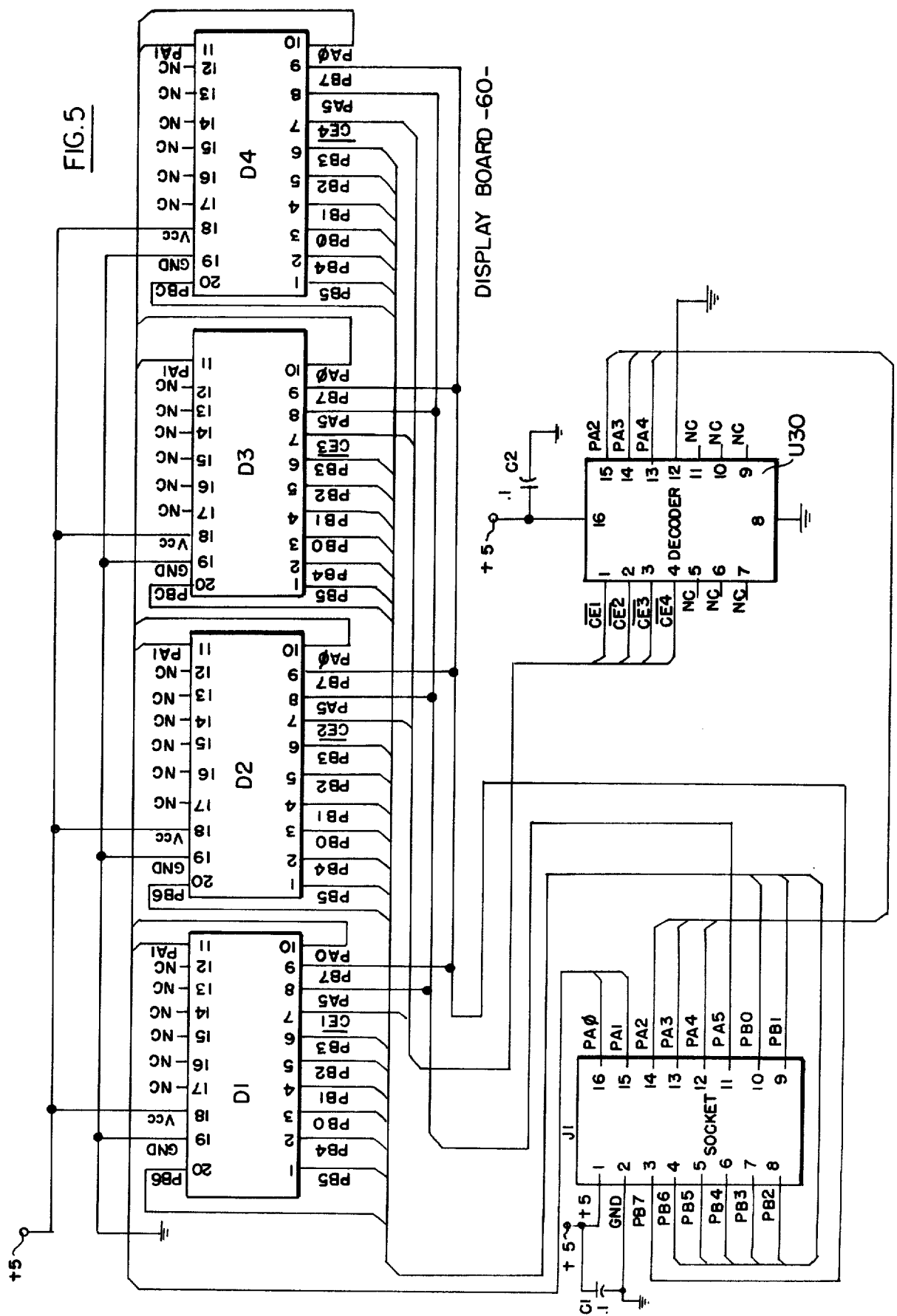
FIG. 5 is a circuit diagram of an alphanumeric display which is included in the data analyzing system.

The circuit for the display board 60 of FIG. 3 is shown in FIG. 5. The circuit of FIG. 5 includes four self-contained displays D1, D2, D3 and D4, each of which is of the type designated DL1416. The display units are selected by a decoder U30 of the type designated 74LS42. The drive signals for the display boards designated PA0–PA5, PB0–PB7, are received from the connector J1, which is connected by an appropriate cable to connector J5 of the circuit of FIG. 9B.

Figure 9B:
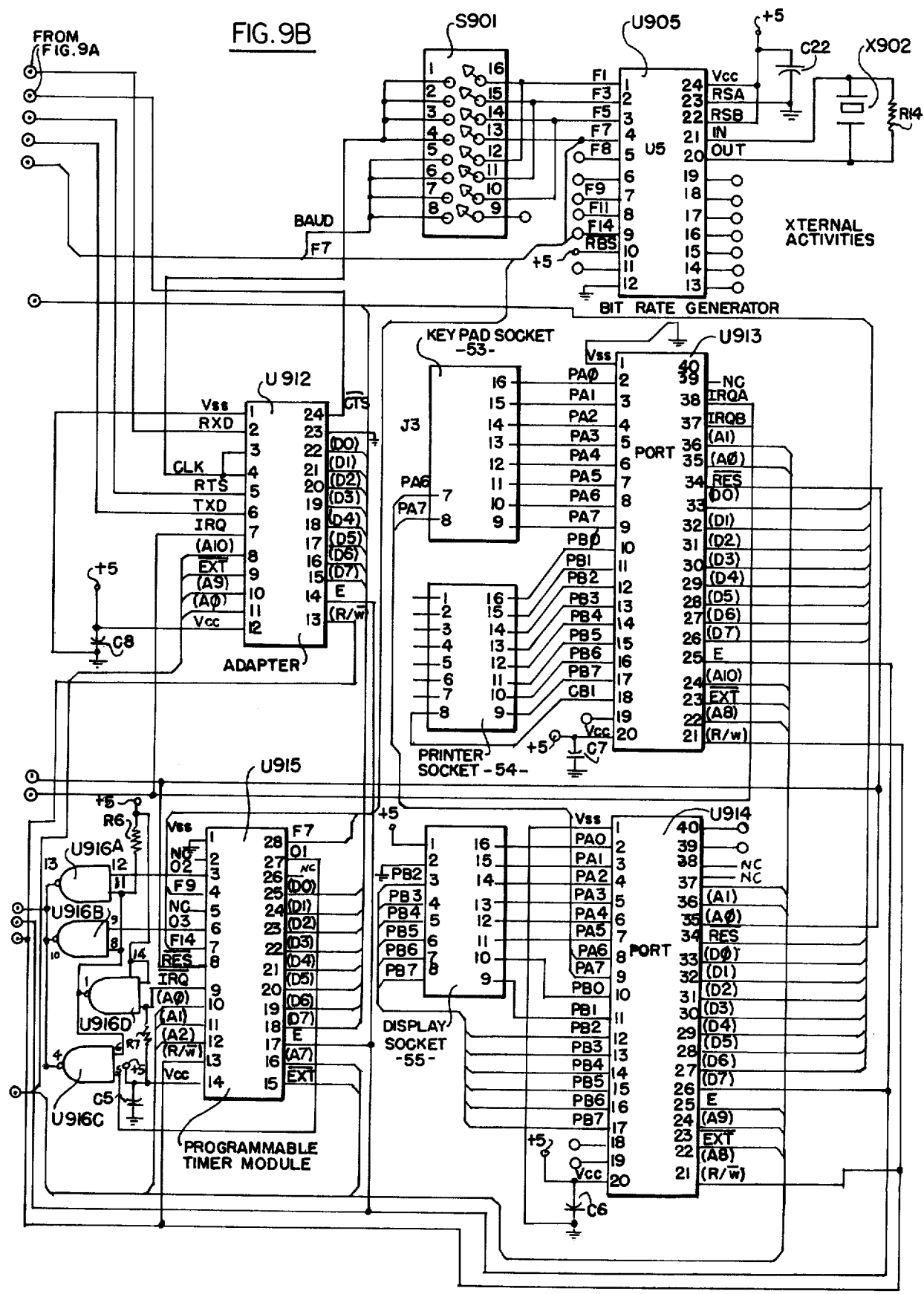

The signals PA0 through PA7 and PB0 through PB7 are drive signals received from a peripheral interface adapter chip U914 in FIG. 9B by way of a connector J5. The P stands for peripheral, the A stands for the A side of the chip, and 0 through 7 stands for the bit count; and the PB signals are derived from the B side of the chip. There is a total of 16 bit capability on a peripheral interface adapter U914 to interface to the 8 bit data line ($D_0$–$D_7$).

Each unit D1–D4 of the display 60 contains four characters, and there are four units. The decoder U30 selects which of the four units is to be activated; the PA signals select which character in the selected unit is to be energized; and the PB signals determine the format of the selected character.

The interface circuit from the data analyzer system of the invention to the ABA-100 is shown in FIG. 6. The cable 52 of FIG. 1 is connected to two peripheral interface adapters U40, U41, which are general purpose input/output integrated circuits of the type designated MC6821. The interface circuit of FIG. 6 also includes two random access memories designated U43 and U44, each of which may be of the type designated M2114, and a decoder U46 for the memories which may be of the type designated 74LS139. A pair of receivers U48 and U50, each of which may be of the type designated 74LS244, receive address signals A0–A11, as well as a RESET signal, and signals R/W, E, VMA, from the circuitry of FIG. 9B.

The circuit of FIG. 6 also includes a pair of transceivers designated U51 and U52 which receive and transmit data signals D0–D7 from and to the circuit of FIG. 9B. The transceivers U51 and U52 may be of the type designated 8T26A.

Steering logic circuitry is associated with the transceivers U51 and U52, and this circuitry includes "nand" gates U8c, U8d, U13a, U13b and U13; and "nor" gates U19c and U19d. The "nand" gates may be of the type designated 74LS10, and the "nor" gates may be of the type designated 74LS02.

Each interface adapter U40 and U41 is connected to sixteen input/output lines entitled PA0–PA7 and PB0–PB7; and each peripheral interface adapter is connected to four additional lines two of which are for input only and are used for detecting interrupts; and two of which are for input or output and are used for either detecting interrupts on the input or for signalling that something is about to take place. The additional lines are designated CA1A, CA2A, CB1A, CB2A, and CA1, CA2, CB1, CB2 respectively.

The interface to the ABA-100 insures that the data present at the ABA-100 is collected by the data analyzing system of the invention at the appropriate times.

The data transmitted from the ABA is first buffered in the interface circuit of FIG. 6. This insures that the integrity of the data will be maintained from the time it is received from the ABA-100 until the time it is actually used by the data analyzing system of the invention. For that purpose the interface circuit has a separate RAM capability (U43,U44) beyond the RAM capability of the data analyzing system itself. Decoder U46 establishes whether or not a read or write operation is going to take place to the RAM's, or to either one of the peripheral interface adapters U47, U48.

The entire interface circuit of FIG. 6 is selected by slot select signal (SSA) unlike the rest of the system which is addressed by pure address lines. This means that several interface circuits can be used to interface the data analyzing system independently to different ABA-100's, or other external devices.

Essentially the slot select signal is defined as a signal that activates the particular interface circuit, independently of any other interface circuit in the same address location. Consequently, one may interface the data analyzing system to the ABA-100 and to another device (whether it be a medical device or whether it be a display) and use the same address space in both cases. The use of the slot selection signal allows a 16-bit microprocessor, for example, to address a much larger area of memory than normally. The selection is determined by whether the SSA signal is high or low.

The slot select concept described above is a way of establishing a multitude of 16K or 32K blocks of memory occupying the same memory space at different instants of time. If the microprocessor is capable, for example, of addressing 64,000 bytes of memory, then by use of the slot select it can be capable of addressing independently as many as 225,000 bytes of memory. A means therefore has been established, whereby a particular memory address can occupy the same place in several different circuits.

The circuitry of transistors Q1, Q2 and Q3 is necessary, to interface to the ABA-100 and other external devices with the standard TTL logic used in the data analyzing system.

Figure 7B:
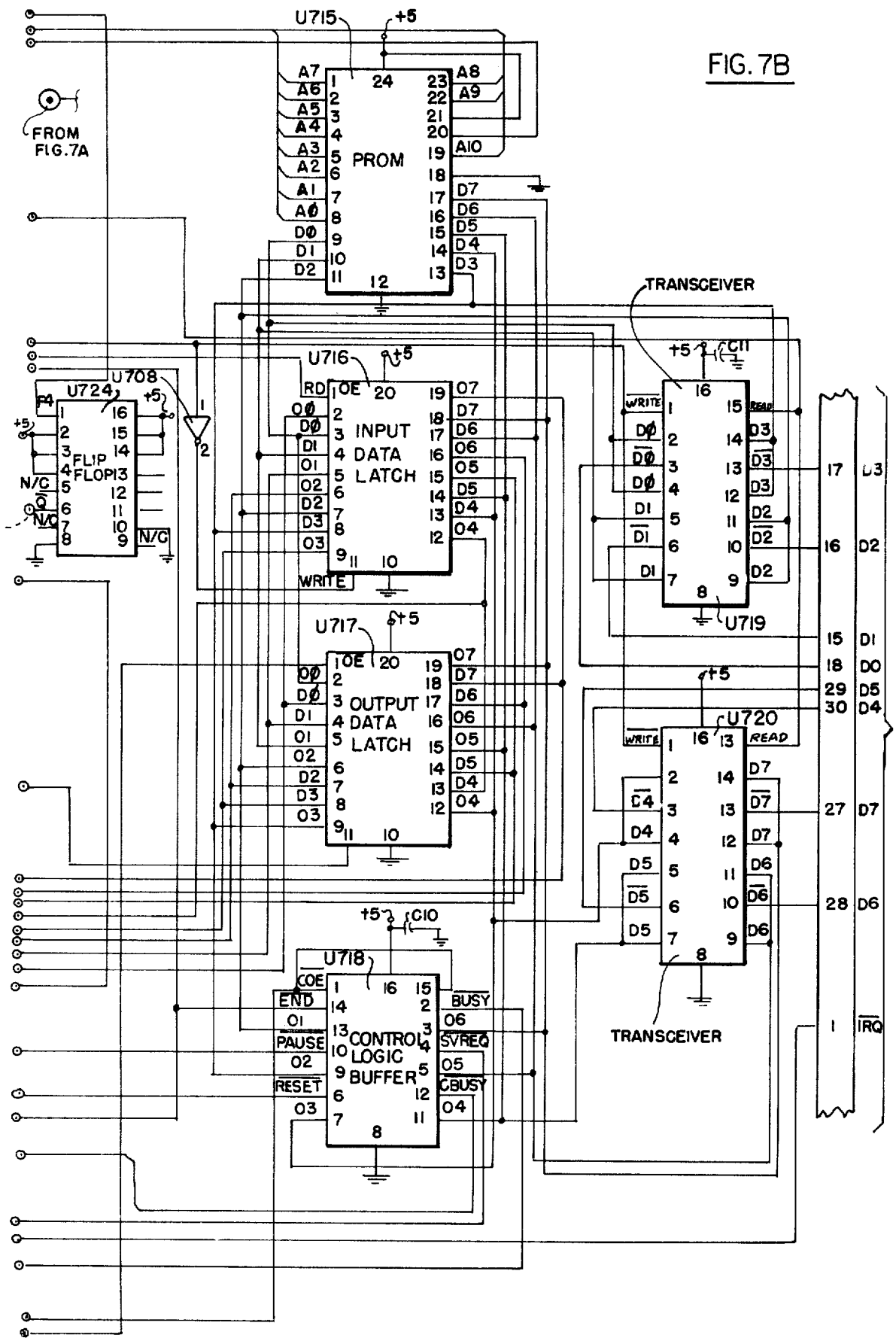

The arithmetic processor circuitry of FIGS. 7A and 7B responds to the absorbance reading signals from the ABA-100 to convert the readings into reportable units, as mentioned above. These conversions may be linear or non-linear, depending upon the particular test, and they are carried out in an arithmetic processing unit integrated circuit designated U714 which is constructed by the Advance Microdevices Company, and which is designated by them as AMD9F11.

The circuitry of FIG. 7A is addressed by address signals from the microprocessor of FIG. 9B, the addresses being received by a plurality of receivers designated U721, U722, U723, each of which may be of the type designated 74LS244. The address signals are decoded in appropriate decoding logic made up of "nand" gates U701, U702, and U704A, U704B and U704C; and "nor" gates U703A, U703B and U703C. The "nand" gates U701 and U702 may be of the type designated 74LS30, the "nor" gates may be of the type designated 74LS02, and the "nand" gates U704A, U704B and U704C may be of the type designated 74LS10.

The read-write command signal $R/\overline{W}$ is received in a buffer U707 which may be of the type designated BT26A, and which is addressed by the address signals $A_0$, $A_1$ and $A_{12}$ from the receivers. Buffer 707 is connected to a pair of "nand" gates U705A and U705B which are controlled to supply read and write signals to a control latch U713 of the type designated 7475, and which is connected to the arithmetic circuit U714. The signals E and VMA are received in a receiver U721 of the type designated 74LS244, and which is connected to the decode logic "nand" gates U701 and U704B. The reset signal $\overline{RESET}$ from the microprocessor is applied to a reset one-shot designated U710 which may be of the type designated 74LS122. The one-shot supplies a reset signal to the arithmetic processing unit U714.

Buffer U707 is also connected to an "and" gate U706 which may be of the type designated 74LS11, and the output of the "and" gate is connected through an inverter U708 of the type designated 74LS04 to a "nand" gate U705C of the type designated 74LS00. The "nand" gate is connected through an exclusive "nor" gate U709A, of the type designated 74LS266, to the control latch U713.

The circuit of FIG. 7A also receives a clock signal F4 which is divided by 2 in a flip-flop U724 of the type designated 74LS112, and which supplies a clock signal to integrated circuit U714. The integrated circuit U714 is also connected through a pair of inverters U708A and U708B which may be of the type designated 74LS04 to "and" gates U706A and U706B which may be of the type designated 74LS11. "And" gate U706A supplies a busy signal $\overline{BUSY}$ to "and" gate U706, and "and" gate U706B is connected to a latch 711 which may be of the type designated 74LS74. The circuit includes a one-shot U711 which may be of the type designated 74LS122. The circuit also includes a decoder U712 which may be of the type designated 74S139, and which is connected to buffer U707.

The circuit of FIG. 7B receives the data signals D0-D7 from the microprocessor of FIG. 9B, and transmits like data signals to the microprocessor over the same bus, and it also transmits the command $\overline{IRQ}$ to the microprocessor. The command signal $\overline{IRQ}$ is derived from an exclusive "nor" gate U709B in the circuit of FIG. 7A, which may be of the type designated 74LS266, and which is connected to the arithmetic integrated circuit U714.

The data signals are received from and transmitted to the microprocessor by transceivers U719 and U720, each of which may be of the type designated 8T26A, with the input data being stored in an input data latch U716, and with the output data being stored in an output data latch U717, each of these latches being of the type designated 74LS373. The latches are connected to the arithmetic integrated circuit U717 in FIG. 7A.

The circuit of FIG. 7B also includes a programmable read-only memory U715 which may be of the type designated 2716, and which is addressed by the address signals received from the circuit of FIG. 7A, the programmable read-only memory (PROM) U715 supplying data signals to the input and output data latches U716, U717.

The circuit of FIG. 7B also includes an integrated circuit U718 of the type designated 8T98, and which serves as a control logic buffer. This circuit receives a signal $\overline{SVREQ}$ from an inverter U705 which may be a "nand" gate of the type designated 74LS00, and which serves to invert the signal $\overline{SVREQ}$ received from integrated circuit U714. Also, the input data latch U716 receives the write signal from the control latch 713 of FIG. 7A by way of an inverter U708 which may be of the type designated 74LS04.

The arithmetic processing circuit of FIGS. 7A and 7B is designed to allow the data analyzing system of the invention to take advantage of the capabilities of the integrated circuit U714, which in essence is a microprocessor in its own right. Essentially several bytes of data are introduced to the circuit in the form of bits that represent numbers, and the circuit functions very much like a calculator. That is a series of numbers are fed into the circuit, and then a command is given to manipulate the numbers in a particular way, that is to multiply them, or to add them, or to take them to the power of $-27.6$, or whatever is desired. In essence data is fed to the circuit, and then a command is introduced, and then the information is retrieved which is the result of the manipulation of the numbers ordered by the command.

That is, the arithmetic processing circuit of FIGS. 7A and 7B performs the mathematical functions of the data analyzing system in much the same way as one would physically manually punch the keys on a calculator. The circuit does not, however, instruct the data analyzing system as to what sequence of mathematical operations should occur for a particular circumstance, rather it just simply provides the mathematical power to manipulate the numbers in whatever manner the rest of the data analyzing system tells it to do so.

Looking at FIG. 7A, there are usual receivers U721, U722, U723 for the addresses, and connected to the receivers are the "nand" and "nor" gates U701-U704 which form the address decode logic. The one-shot U710 provides a reset pulse to the arithmetic processing unit U714. This unit can be caused to reset either by the system reset ($\overline{RESET}$), which triggers the one-shot, or by a command from an instruction that tells it to reset.

Now moving over to FIG. 7B, there are the usual transceivers U719, U720 for the data, and the input and output data latches U716 and U717, and the control logic buffer U718. The PROM U715 contains the necessary software to facilitate passing data back and forth between the arithmetic processing circuit of FIGS. 7A and 7B, and the rest of the system. It contains, for example, the appropriate instructions to perform a standard linear regression. Essentially a set of numbers are placed in memory on which a linear regression is to be performed, and then a routine stored in the PROM U715 is used to manipulate these numbers and to return to a given location of memory the result of that linear regression. The PROM U715 in general contains the appropriate instructions necessary to manipulate the arithmetic processing unit U714. This is because the data fed to the arithmetic processing unit U714 must be in the proper format, and must be put into the arithmetic processing unit in the proper sequence. This requirement is taken care of by instructions set in the PROM U715.

The floppy disc controller circuitry, as stated above, is shown in FIGS. 8A and 8B. This circuitry, as shown in FIG. 8B includes an integrated circuit 806, of the type manufactured by Western Digital Corporation, and designated by them FD1793, and which serves to control the floppy disc.

One megahertz clock signals are supplied to the controller by dividing by four the 4 megahertz master clock of the system. A one-shot U801B is also connected to the controller, and this one-shot may be of the type designated 74LS221.

The circuitry of FIG. 8B includes decoding logic circuitry for the controller U806, and which is made up of a series of "nand" gates U803A, U803B, U803C, of the type designated 74LS10; inverters U805A, U805B, U805C and U805D of the type designated 74LS04; and "nor" gates U802A, U802B and U802C of the type designated 74LS02. A write enable delay one-shot U801A, of the type designated 74LS221, is also included in the logic circuitry. The decoding logic circuitry responds to the signals A$_7$, $\overline{SSA}$, R/$\overline{W}$ and E to provide appropriate control signals for the controller U806. The address signals A$_0$ and A$_1$, as well as the reset signal RESET are also applied to the controller U806.

The controller supplies a signal designated IRQ back to the circuitry of FIG. 9 by way of an NPN transistor Q801, which may be of the type designated 2N2222. Data signals D0–D7 are received from the circuit of FIG. 9B, and transmitted to the controller U806 by way of transceivers U807 and U808 in FIG. 8A, which may be of the type designated 8T26A, and the aforesaid logic decoding circuitry is connected to the transceivers through steering logic "nand" gates U804A and U804B of the type designated 74LS10, and through an inverter U805D of the type designated 74LS04.

The floppy disc controller U806 is connected to buffers formed by "nand" gates U809A, U809B, U809D and U810A, which may be of the type designated 74LS38, and to a series of buffers U810C, U810D, U809C and U810B, which also are "nand" gates of the type designated 74LS38. A latch U820 of the the type designated 74LS125 is also connected to the buffers. The buffers are connected to an output connector designated J2, and they supply various control signals to the floppy disc drive 62 of FIG. 3. The connector J2 is also connected to buffers formed of inverters U811A, U811B, U811C, U812A, U812B and U812C to supply signals WPT, IDX, TKOO to the floppy disc controller.

The floppy disc controller U86 is a processing unit which serves to interface the circuitry of the data analyzing system with the external floppy disc drive 62 of FIG. 3. However, the controller U806 is not so designed that there is involved merely the simple process of simply plugging in the controller and connecting wires to the central processing unit of the data analyzing system and to the floppy disc drive. In the prior art systems a significant amount of hardware was required to interface the controller to the central processing unit. The major portion of the hardware was required because of an incompatability in timing between the central processing unit and the floppy disc controller U806. By using timing devices in the input to the controller U806, the need to add the extra integrated circuits, such as a peripheral interface adapter is obviated, and the interface into the central processing unit is thereby made much simpler.

Essentially the read and write functions to the floppy disc controller U806 timing-wise are incompatible with the central processing uinit. However, by using the one-shot on the U801A write enable (E) pulse, the write signal is speeded up in reference to the rest of the system. Consequently, the interface can take place directly to the central processing unit bus without the addition of extra hardware.

The floppy disc controller U806 requires a clock of 1 megacycle to interface to the 5¼ inch mini-floppy disc drive 62 of FIG. 3. In lieu of adding an additional crystal and associated circuitry to generate that clock; the 4 megahertz master system clock is divided down by flip-flop U813B thereby to achieve a 1 megahertz clock to drive the floppy disc controller.

The floppy disc used in the system is a single sided, single density 5¼ inch disc. The test files are recorded on the floppy disc. These files define the parameters of the particular tests to be carried out by the ABA-100, in alphamumeric format to designate, for example, whether the test is glucose, BUN, or some other test. Specific entities or attributes of the individual tests such as the reaction direction, the type of test, the calibrate factor or RAH factor if one is involved, are also recorded on the disc. In addition, the normal ranges, the controls, the standards, etc., for the various tests are recorded on the disc.

Also stored on the disc is an accumulative data file of values such that the customer can establish whether or not the quality control of the entire system is at a proper level. In addition there are program texts, or overlays, stored on the disc. By using overlay program sources stored on the disc one can create a large number of blocks of program memory by overlaying one block on top of another. There is also stored on the disc a file containing the total data from a given run from the ABA-100 to allow the customer to accumulate results from four or five different runs and print out those results in an accumulative manner.

For example, if one wishes to run a glucose test, there are specific requirements in terms of timing, in terms of the kind of mathematics that are to be performed, and essentially in the sequence of events that occur to run a glucose test. All the instructions for the central processing unit that tell it what to do are stored on the disc in a particular file. That file instructs the central processing unit how to run a test, such as glucose, which is defined as an end-point type of reaction. On the other hand if one wishes to run a non-linear chemistry, such as primidone, where the instruction sequence is essentially different, instructions to the central processing unit are stored in a different file on the disc.

When one calls up any selected test, by pressing the appropriate keys on key pad 56 of FIG. 1, then the appropriate instruction text for that test is loaded from the disc into the data analyzing system random access memory. For example, if one selects the glucose test on the key pad, a corresponding instruction text is loaded into the RAM. On the other hand, if one calls up the test for primidone on the key pad, a different set of instructions are loaded into the system RAM. Consequently, although the data analyzing system itself is limited, for example, to 8K bytes of random access memory, there is enough room on the disc to permit several blocks of 8K worth of instructions to be stored, so that the virtual capability of the data analyzing system goes beyond that of the 8K.

At the lower left-hand corner of FIG. 8A, there is a connector J2 which connects with the floppy disc drive. The line coming from the connector labelled "read data", carries data read from the floppy disc. Also the line entitled "WD" carries write data to the disc. Although the system is presently using a single-sided disc, the system is capable of handling a two-sided disc drive, and in that case the SIDE SEL line is used to select which side of the disc is to be used for reading or writing.

The line TKKOO from connector J2 carries a signal from the disc that tells the data analyzing system that the read/write head is positioned over track 0, which is the starting point. The line WG (write gate) carries a signal from the floppy disc controller U806 to the disc drive that tells the disc drive that the system is about to write data, and this signal allows the read/write electronics in the disc drive to stabilize. The line designated STP (step) carries a signal from the floppy disc controller U806 to the disc drive that tells the disc drive to step the read/write head forward by one track, from track 0 to track 1, and so on, in either direction. The next line is designated DIR (direction), and it carries a signal which determines which direction the read/write head is going to move in response to the step signal.

The line MOTOR ON carries a signal to the disc drive that turns on the motor which drives the disc, and this signal also enables the read/write electronics in the disc drive. The lines designated DRV SEL 1 and DRV SEL 2 enables either one of two independent disc drives to be selected. The line designated IDX (index pulse) enables the floppy disc controller U806 to locate the beginning of each track on the disc. This track origin position is denoted by a hole in the disc, and the IDX line goes high when the read/write head is positioned at the beginning of that track.

In the operation of a floppy disc of the single density type, a clock pulse is received to indicate the beginning of a bit cell. Then some period of time later, either a "1" or a "0" appears to indicate whether or not that bit cell is a "1" or a "0", and then another clock pulse appears, and so on. For every eight clock pulses four bits of data are received. The floppy disc controller U806 cannot distinguish when clock and data bits are missed together because it cannot determine which is a clock bit and which one is a data bit.

The circuitry of integrated circuits U813A, U814B, U814A, U811, makes up the data separator circuit. This circuit essentially strips away the data pulses from the clock pulses, and it transmits the clock pulses by themselves to one of the pins of the floppy disc controller U806, and it transmits clock and data pulses to another pin, thereby enabling the floppy disc chip to determine which pulse is data and which pulse is clock. The clock pulses (RCLK) are applied to pin 26, and the data and clock pulses ($\overline{\text{RAW RD}}$) are applied to pin 27 of the controller U806. The data separator circuit in the upper portion of FIG. 8A serves to separate the clock from the data, and it supplies the read clock (RCLK) to the controller and it also supplies raw data ($\overline{\text{RAW RD}}$) which has data and clock to the controller.

There are certain physical constraints in timing for the particular controller U806, and the data separator in addition to separating the data, helps shape the pulses so that they are adequately understood by the controller. So then a portion of the circuit at the top of FIG. 8A strips the clock from the raw read signals from the floppy disc.

When the data and clock signals are written into the floppy disc, the information occurs in a series of clock and data pulses, and the period of time in which the data pulse appear is exactly a predetermined amount from a corresponding clock pulse in each case. However, when the data and clock signals are subsequently read from the disc, the foregoing period of time may vary in successive data cells because of variations in disc speed.

If the clock frequency of the data read from the disc is the same as the frequency of the pulse signal from the voltage controlled oscillator U818, then the signals generated by the flip-flops U815A and U815B are such that transistors Q1 and Q2 are equally conductive and the voltage controlled oscillator frequency is unchanged. However, if the clock frequency of the data from the disc increases or decreases, the conductivity of either transistor Q1 or Q2 increases, and the frequency of the voltage controlled oscillator is changed until it again matches the clock frequency of the data read from the disc.

The output of the voltage controlled oscillator is introduced to flip-flop U814B which generates the RAW READ signal for controller U806. The output of the flip-flop U817 is introduced to flip-flop U813A which generates the clock signal RCLK for controller U806.

For all intent and purpose, raw read signal $\overline{\text{RAW READ}}$ and read clock RCLK are not actually coming from the disc itself, but are generated by the phase-loop circuitry, the only difference is the read clock RCLK speed is dictated by the circuitry. Then as a bit cell comes through, if the bit cell was zero within the constraints of some movement between the clock pulses, that zero or one is essentially transmitted through the circuitry. But it's not actually the same pulse, it is a pulse generated by the circuitry itself, so it is square shaped and has a finite width.

The read clock RCLK is generated by flip-flop U813A and the raw read signal $\overline{\text{RAW READ}}$ is being generated by flip-flop U814B, and these two flip-flops are under the control of the phase locked loop circuit and the incoming data. Therefore, the RCLK clock pulses change as the speed of the floppy disc changes, and the floppy disc controller U806 is kept in synchronism.

The incoming address signals going through the decode logic U802A, U802B, U802C, U803A, U9803B, U803C determine whether the floppy disc, controller U806, or the latch U820 is addressed. The latch U820 is essentially an interface adapter, it allows data to be taken from the data line of the central processor unit and send to peripheral devices. In this case the data signals are in the form of a drive select, motor on, and side select signals. The latch U820 is required because the controller U806 is incapable of generating signals such as "motor on", "drive select", "side select", and the like.

Without the one-shot U801A, a peripheral interface adapter would be required because the timing considerations of the central processor side of the floppy disc controller U806 are such that the controller cannot be directly interfaced to the central processing unit. However, such an adapter is a 40-pin expensive integrated circuit chip. The one-shot U801A obviates the need for a peripheral interface adapter, thereby cutting down the integrated circuit chip count and, making the overall circuitry more efficient, more responsive to temperature and temperature changes.

Essentially, the floppy disc controller U806 requires that when data is to be presented to its data lines, its read/write line (R/W) must fall some 400 nanoseconds before the data becomes invalid again. This is not consistent with the central processing unit which dictates that the data will be maintained valid for some 20 nanoseconds after the fall of the write enable pulse. By using the one-shot U801A, the write enable pulse is shortened in time allowing the hold time requirements of the floppy disc controller chip to be met. This precludes the need to latch the data from the central processing unit into a peripheral interface adapter, and the need for yet another step of sending the latched data to the floppy disc controller U806. The addition of the one-shot U801A thereby eliminates two extra steps in software to communicate back and forth between the floppy disc controller U806 and the central processing unit, so that in essence the reduction in integrated circuit chip count and complexity is significant.

As mentioned above, the central processing unit microprocesor circuit is shown in FIGS. 9A and 9B. The circuitry of FIG. 9A includes a microprocessor designated U911, which may be of the type designated MC6800P. The microprocessor generates the address signals $A_0$–$A_{15}$ through address drivers designated U817 and U818, which may be of the type designated 74LS244; and the microprocessor is controlled by three programmable read-only memories U919, U920 and U921, which may be of the type designated 2716. Clock signals for the microprocessor are generated by a crystal controlled oscillator including integrated circuit U910 of the type designated MC6875P, and which is controlled by a 4 MHz crystal X901. Also included in the microprocessor circuit is a latch U925, of the type designated 8%26A; a latch U922 of the type designated 74LS373, and an address decode circuit U924 of the type designated 74LS138. "Nand" gates U923A, U923B, U923C and U923D of the type designated 74LS00 are connected to these circuits.

The latch U922 is used to establish a slot select function. Address line A15 is used as a determining factor for the slot select function. The slot select function permits 32,000 bytes of memory per slot to be set aside, and there is a total of 8 slots in a constructed embodiment of the invention, so that 8×32,000 memory locations can be addressed. Basically, the software of the system tells it to select a given slot. Once that selection has been made, the main memory may still be used, so that 32K block of additional memory may be combined with the main memory.

The circuitry of FIG. 9A also includes a pair of transceivers U908 and U909, which may be of the type designated 8T26A, and logic circuitry is connected to the transceivers and to a connector J2. Data passing to and from the data analyzing system by way of the connector J2 passes through these transceivers. The logic circuitry connected to the transceivers includes a series of "nand" gates designated U903A, U903B, U904A, U904B, U904C and U904D; of the type designated 74LS00. The logic circuit also includes "nand" gates U907A, U907B, U907C and U907D, also of the type designated 74LS00; and the circuit includes a number of inverters U902A, U902B, U906A, U906B and U906C. Finally, the logic circuitry includes an integrated circuit U901 of the type designated 4N33, an NPN transistor Q902 of the type designated 2N2219, and a PNP transistor Q901 of the type designated 2N2905.

The circuit of FIG. 9B includes a bit rate generator circuit which is controlled by a crystal X902, and which includes a divider circuit U905 of the type designated 14411. The generator also includes a switch S901 which is used to select a desired clock frequency from the generator. This permits the data analyzing system to generate clock signals at different Baud rates to adapt it to interface with computers of a variety of different Baud rates.

Also included in the circuit of FIG. 9B is a peripheral interface adapter integrated circuit chip U913 of the type designated MC6821P which receives data and other control signals for controlling the printer 58 and for responding signals from the key pad 50. A peripheral interface adapter integrated circuit chip U914 is also included in the circuit which provides control signals for the display 60 of FIGS. 1 and 3. A synchronizing interface adapter circuit U912 of the type designated MC6850P is included in the circuit for controlling external devices. A programmable timer module U915 for synchronizing the data analyzing system with the ABA-100 is also included in the circuit. "Nand" gates U916A, U916B, U916C and U916D are connected to the module U915, and may be of the type designated 74LS01, and these "nand" gates supply the signal $\overline{NMI}$ to the microprocessor U911 of FIG. 9B.

The adapter U912, and the logic circuitry at the top of FIG. 9A including the connector J2 are used to interface the data analyzing system with another computer. This permits, for example, data to be sent from the data analyzing system to a central computer, that is, it affords the capability of interfacing the data analyzing system to the central computer.

The asynchronous communication adapter U912 is a serial device analagous to the peripheral interface adapter which is a parallel device. The logic circuitry on the upper portion of FIG. 9A is a driver circuit associated with the asynchronous communication adapter U912. The actual data comes from the asynchronous communication adapter, and it is buffered by the logic circuitry to bring it up to the levels, i.e., ±12 volts necessary for standard communication exchange between computers. Specifically, adapter U912 responds to parallel data and converts it into serial data to be fed to the external computer, and vice versa.

The programmable timer module U915 is essentially the heart of the real time clock used in the data analysis system. The timer module U915 is used by the data analyzing system for interfacing to the ABA-100. The programmable timer provides three independent internal timers. One of the timers is driven by the 60 cycle line because the ABA-100 receives its timing from the 60 cycle line. If, for example, the 60 cycle line frequency were to change by say 2%, then the timing between the data analyzing system and the ABA-100 would get out of synchronism if the data analyzing system were not also tied to the 60 cycle line. The advantage of using a real time clock in conjunction with the ABA-100 allows the data analyzing system to take advantage of certain data that is available from the ABA-100, of which other prior art systems cannot. The prior art systems must use a print pulse that comes from the ABA-100 to establish that it is time to look at data. That precludes the use of data generated by the ABA-100 at any other time. There is rather meaningful data generated by the ABA-100 prior to the time at which print command pulses are available, such data being used, for example, for serum blanking. Consequentgly, the use of a real time clock in the data analyzing system permits it to gain access to information from the ABA-100 to be further used in processing data that allows it to give more accurate and more precise results.

The invention provides, therefore, a microprocessor controlled data analyzing system which may be coupled to a clinical spectrophotometer, such as the Abbott ABA-100, and which is capable of providing the operator with full instructions as to any particular test and to control the spectrophotometer to perform such a test.

While a particular embodiment of the invention has been described, modifications may be made, and it is intended in the following claims to cover all such modifications which come within the true spirit and scope of the invention.

What is claimed is:

1. A data analyzing system for controlling the operation of a clinical spectrophotometer to enable the spectrophotometer to conduct a plurality of different assays and for directing the sequence of operations of the spectrophotometer for any particular assay, and for analyzing analog output data signals received from the spectrophotometer representing the results of such assays, said data analyzing system including: a microprocessor circuit; an interface circuit connected to the microprocessor circuit and to the spectrophotometer for interconnecting the data analyzing system to the spectrophotometer to introduce the output signals from the spectrophotometer to said microprocessor and to introduce control signals from the microprocessor to the spectrophotometer; an arithmetic processor circuit connected to the microprocessor and controlled thereby for calibrating the results of the assays made by the spectrophotometer and for converting the results into reportable units; a keyboard connected to the microprocessor circuit for enabling an operator to enter signals into the microprocessor representing the code number corresponding to a selected assay; an alphanumeric display panel connected to the microprocessor and responsive to signals from the microprocessor for displaying the name of the assay selected by the keyboard; a disc memory drive system connected to the microprocessor for storing information representing the particular assays to be performed by the spectrophotometer and for introducing signals to the microprocessor representing the sequence of operations of the particular assay selected by the keyboard to cause the microprocessor to introduce corresponding control signals to the spectrophotometer through said interface circuit; a printer circuit connected to the micrporocessor circuit and responsive to signals therefrom for printing out various settings of the spectrophotometer corresponding to the sequence of operations to be performed thereby in accordance with the particular test selected by the keyboard to be established for the selected assay, and further responsive to signals from the microprocessor representing calculations by said arithmetic processor circuit for printing out data relating to absorbance readings by the spectrophotometer in laboratory reportable units.

2. The data analyzing system defined in claim 1, in which the information stored in said disc memory includes data pulses and clock pulses, and which includes circuit means coupling said disc memory to said microprocessor circuit which includes circuitry for separating out the clock pulses from the data pulses and for introducing signals representing the separated clock pulses to said microprocessor circuit.

3. The data analyzing system defined in claim 1, and which includes a random access memory circuit connected to said microprocessor circuit for storing data to be processed by the system, and which includes slot-selection circuitry connected to said microprocessor circuit and to said random access memory circuit for introducing a slot signal to said random access memory circuit to enable the microprocessor circuit to address memory locations in excess of the memory addressing capabilities of the random access memory circuit.

4. The data analyzing system defined in claim 1, and which includes further interface circuitry connected to the microprocessor circuit for interfacing the data analyzing system with a remote computer having a particular clock frequency for the transmission of data signals to the remote computer, and in which said further interface circuitry includes a bit rate generator for generating clock signals at different Baud rates, and manually adjustable circuitry connected to the bit rate generator for controlling the Baud rates of the clock signals generated by the bit rate generator to enable the bit rate generator to produce clock signals at a selected Baud rate matching the clock frequency of the remote computer.

* * * * *